United States Patent
Buffa et al.

(10) Patent No.: US 9,522,966 B2
(45) Date of Patent: Dec. 20, 2016

(54) HYALURONIC ACID DERIVATIVE, METHOD OF PREPARATION THEREOF, METHOD OF MODIFICATION THEREOF AND USE THEREOF

(71) Applicant: Contipro Biotech s.r.o., Dolni Dobrouc (CZ)

(72) Inventors: Radovan Buffa, Humenne (SK); Petra Sedova, Ceska Trabova (CZ); Vladimir Velebny, Zamberk (CZ); Lucie Wolfova, Opava (CZ); Ivana Basarabova, Medzilaborce (SK); Robert Pospisil, Spojil (CZ); Martina Hasova, Letohrad (CZ); Kristina Nesporova, Brno (CZ)

(73) Assignee: Contipro Biotech s.r.o., Dolni Dobrouc (CZ)

( * ) Notice: Subject to any disclaimer, the term of this patent is extended or adjusted under 35 U.S.C. 154(b) by 47 days.

(21) Appl. No.: 14/420,012

(22) PCT Filed: Aug. 5, 2013

(86) PCT No.: PCT/CZ2013/000091
§ 371 (c)(1),
(2) Date: Feb. 6, 2015

(87) PCT Pub. No.: WO2014/023272
PCT Pub. Date: Feb. 13, 2014

(65) Prior Publication Data
US 2015/0175717 A1 Jun. 25, 2015

(30) Foreign Application Priority Data

Aug. 8, 2012 (CZ) ...................................... 2012537

(51) Int. Cl.
*A61K 47/48* (2006.01)
*C07K 17/10* (2006.01)
(Continued)

(52) U.S. Cl.
CPC ....... *C08B 37/0072* (2013.01); *A61K 47/4823* (2013.01); *C07K 17/10* (2013.01); *C08J 3/075* (2013.01); *C08J 2305/00* (2013.01)

(58) Field of Classification Search
None
See application file for complete search history.

(56) References Cited

U.S. PATENT DOCUMENTS 3,720,662 A 3/1973 Tessler et al.
3,728,223 A 4/1973 Kaneko et al.
(Continued)

FOREIGN PATENT DOCUMENTS

CA 2512730 A1 7/2004
CH 628088 A5 2/1982
(Continued)

OTHER PUBLICATIONS

Akkara, J. A.. et al., "Synthesis and characterization of polymers produced by horseradish peroxidase in dioxane," Journal of Polymer Science Part A: Polymer Chemistry 1991, 29 (11), 1561-1574.
(Continued)

*Primary Examiner* — Layla Berry
(74) *Attorney, Agent, or Firm* — Wood Herron & Evans LLP

(57) ABSTRACT

The invention relates to the preparation and use of α,β-unsaturated aldehyde of hyaluronan having a double bond in the positions 4 and 5 and an aldehydic group in the position 6 of the glucosamine part of the polysaccharide. The method of preparation is based on dehydration of hyaluronan having an aldehydic group in the position 6 of the glucosamine part of the polysaccharide. Two methods have been described, which are dehydration in a solution or heating in solid state in absence of solvents, bases or other additives. This derivative allows stabilization of conjugates of hyaluronan with amino compounds by means of a multiple bond from the aldehyde side, and therefore, it is possible to effectively immobilize practically any compound containing an amino group to such modified hyaluronan in physiological conditions. In case of using a diamine or compounds or polymers containing three or more amino groups, it is possible to prepare crosslinked hyaluronan derivatives. The described solution brings along a significant advantage not only in the field of carriers of biologically active substances, but also in tissue engineering where crosslinking with biologically acceptable amino compounds in physiological conditions is very much demanded.

16 Claims, 1 Drawing Sheet

(51) Int. Cl.
*C08B 37/08* (2006.01)
*C08J 3/075* (2006.01)

(56) References Cited

U.S. PATENT DOCUMENTS

| | | |
|---|---|---|
| 4,205,025 A | 5/1980 | Hart et al. |
| 4,258,134 A | 3/1981 | Yoshida et al. |
| 4,713,448 A | 12/1987 | Balazs et al. |
| 4,761,401 A | 8/1988 | Couchman et al. |
| 4,851,521 A | 7/1989 | Della Valle et al. |
| 4,965,353 A | 10/1990 | Della Valle et al. |
| 5,455,349 A | 10/1995 | Grasshoff et al. |
| 5,520,916 A | 5/1996 | Dorigatti et al. |
| 5,550,225 A | 8/1996 | Philippe |
| 5,616,568 A | 4/1997 | Pouyani et al. |
| 5,658,582 A | 8/1997 | Dorigatti et al. |
| 5,676,964 A | 10/1997 | Della Valle et al. |
| 5,690,961 A | 11/1997 | Nguyen |
| 5,824,335 A | 10/1998 | Dorigatti et al. |
| 5,868,973 A | 2/1999 | Muller et al. |
| 6,025,444 A | 2/2000 | Waki et al. |
| 6,075,066 A | 6/2000 | Matsuda et al. |
| 6,288,043 B1 | 9/2001 | Spiro et al. |
| 6,509,039 B1 | 1/2003 | Nies |
| 6,613,897 B1 | 9/2003 | Yatsuka et al. |
| 6,632,802 B2 | 10/2003 | Bellini et al. |
| 6,673,919 B2 | 1/2004 | Yui et al. |
| 6,683,064 B2 | 1/2004 | Thompson et al. |
| 6,719,986 B1 | 4/2004 | Wohlrab et al. |
| 6,902,548 B1 | 6/2005 | Schuler et al. |
| 6,953,784 B2 | 10/2005 | Thompson et al. |
| 7,214,759 B2 | 5/2007 | Pacetti et al. |
| 7,550,136 B2 | 6/2009 | Warner et al. |
| 7,680,038 B1 | 3/2010 | Gourlay |
| 2002/0026039 A1 | 2/2002 | Bellini et al. |
| 2002/0076810 A1 | 6/2002 | Radice et al. |
| 2003/0163073 A1 | 8/2003 | Effing et al. |
| 2003/0205839 A1 | 11/2003 | Bachrach |
| 2004/0101546 A1 | 5/2004 | Gorman et al. |
| 2004/0192643 A1 | 9/2004 | Pressato et al. |
| 2005/0266546 A1 | 12/2005 | Warner et al. |
| 2006/0046590 A1 | 3/2006 | Chu et al. |
| 2006/0084759 A1 | 4/2006 | Calabro et al. |
| 2006/0189516 A1 | 8/2006 | Yang et al. |
| 2006/0281912 A1 | 12/2006 | James et al. |
| 2007/0149441 A1 | 6/2007 | Aeschlimann et al. |
| 2007/0202084 A1 | 8/2007 | Sadozai et al. |
| 2008/0063617 A1 | 3/2008 | Abrahams et al. |
| 2008/0124395 A1 | 5/2008 | Chen et al. |
| 2009/0252810 A1 | 10/2009 | Tommeraas et al. |
| 2010/0172892 A1 | 7/2010 | Uvarkina et al. |
| 2010/0247908 A1 | 9/2010 | Velev et al. |
| 2010/0310631 A1 | 12/2010 | Domard et al. |
| 2010/0310853 A1 | 12/2010 | Schwiegk et al. |
| 2010/0316682 A1 | 12/2010 | Chen et al. |
| 2011/0200676 A1 | 8/2011 | Lin et al. |
| 2011/0263724 A1 | 10/2011 | Gurtner et al. |
| 2012/0245323 A1 | 9/2012 | Buffa et al. |
| 2012/0264913 A1 | 10/2012 | Buffa et al. |

FOREIGN PATENT DOCUMENTS

| | | |
|---|---|---|
| CN | 101897976 A | 12/2010 |
| CN | 102154738 A | 8/2011 |
| CZ | 2006605 A3 | 4/2008 |
| CZ | 20070299 A3 | 2/2009 |
| CZ | 301899 B6 | 7/2010 |
| CZ | 302503 B6 | 6/2011 |
| CZ | 302504 B6 | 6/2011 |
| CZ | 302856 B6 | 12/2011 |
| CZ | 302994 B6 | 2/2012 |
| CZ | 20101001 A3 | 2/2012 |
| CZ | 20120537 A3 | 3/2014 |
| DE | 10331342 A1 | 2/2005 |
| EP | 0161887 A2 | 11/1985 |
| EP | 0216453 A2 | 4/1987 |
| EP | 0763754 A2 | 3/1997 |
| EP | 0554898 B1 | 5/1997 |
| EP | 1369441 A1 | 12/2003 |
| EP | 1454913 A1 | 9/2004 |
| EP | 1115433 B1 | 12/2004 |
| EP | 1538166 A1 | 6/2005 |
| EP | 1217008 B1 | 3/2006 |
| EP | 1826274 A1 | 8/2007 |
| EP | 1905456 A1 | 4/2008 |
| EP | 1607405 B1 | 5/2011 |
| EP | 2399940 A2 | 12/2011 |
| JP | 62104579 A | 5/1987 |
| JP | 63044883 A | 11/1988 |
| JP | H0214019 A | 1/1990 |
| JP | H0625306 A | 2/1994 |
| JP | 2004507586 A | 3/2004 |
| JP | 2007262595 A | 10/2007 |
| JP | 3975267 B2 | 12/2007 |
| JP | 2008208480 A | 9/2008 |
| JP | 2008295885 A | 12/2008 |
| JP | 2010138276 A | 6/2010 |
| KR | 20070118730 A | 12/2007 |
| KR | 20080062092 A | 7/2008 |
| NL | 9700003 A | 7/1997 |
| WO | 9311803 A1 | 6/1993 |
| WO | 9627615 A1 | 9/1996 |
| WO | 9808876 A1 | 3/1998 |
| WO | 9901143 A1 | 1/1999 |
| WO | 9957158 A1 | 11/1999 |
| WO | 0063470 A1 | 10/2000 |
| WO | 0134657 A1 | 5/2001 |
| WO | 0218448 A2 | 3/2002 |
| WO | 0218450 A1 | 3/2002 |
| WO | 0232913 A1 | 4/2002 |
| WO | 0248197 A1 | 6/2002 |
| WO | 02057210 A1 | 7/2002 |
| WO | 2005028632 A2 | 3/2005 |
| WO | 2006010066 A2 | 1/2006 |
| WO | 2006026104 A2 | 3/2006 |
| WO | 2006056204 A1 | 6/2006 |
| WO | 2007003905 A1 | 1/2007 |
| WO | 2007006403 A1 | 1/2007 |
| WO | 2007009728 A2 | 1/2007 |
| WO | 2007033677 A1 | 3/2007 |
| WO | 2008031525 A1 | 3/2008 |
| WO | 2008077172 A2 | 7/2008 |
| WO | 2009037566 A2 | 3/2009 |
| WO | 2009050389 A2 | 4/2009 |
| WO | 2009108100 A1 | 9/2009 |
| WO | 2009148405 A1 | 12/2009 |
| WO | 2010018324 A1 | 2/2010 |
| WO | 2010051783 A1 | 5/2010 |
| WO | 2010061005 A1 | 6/2010 |
| WO | 2010095049 A1 | 8/2010 |
| WO | 2010095052 A2 | 8/2010 |
| WO | 2010095056 A2 | 8/2010 |
| WO | 2010130810 A1 | 11/2010 |
| WO | 2010138074 A1 | 12/2010 |
| WO | 2011014432 A1 | 2/2011 |
| WO | 2011028031 A2 | 3/2011 |
| WO | 2011059325 A2 | 5/2011 |
| WO | 2011059326 A2 | 5/2011 |
| WO | 2011069474 A2 | 6/2011 |
| WO | 2011069475 A2 | 6/2011 |
| WO | 2012089179 A1 | 7/2012 |
| WO | 2012146218 A1 | 11/2012 |
| WO | 2013056312 A1 | 4/2013 |
| WO | 2014023272 A1 | 2/2014 |

OTHER PUBLICATIONS

Aldrich, Chem Files Synthetic Methods Oxidation, May 2005, vol. 5, No. 1 pp. 1-11.
Angelin, M. et al., "Direct, Mild, and Selective Synthesis of Unprotected Dialdo-Glycosides", European Journal of Organic Chemistry, Jan. 1, 2006, pp. 4323-4326.

(56) References Cited

OTHER PUBLICATIONS

Armstrong, D.C. et al., "Culture Conditions Affect the Molecular Weight Properties of Hyaluronic Acid Produced by *Streptococcus zooepidemicus*," Appl. Environ. Microbiol. (1997) 63(7):2759-2764.
Atkins, E.D.T. et al., "The Conformation of the Mucopolysaccharides," J. Biochem vol. 128, 1972, pp. 1255-1263.
Atkins, E.D.T. et al., "The Molecular Structure of Hyaluronic Acid," Biochemical Journal vol. 125, No. 4, 1971, p. 92.
Author unknown, "Readily Accessible 12-I-51 Oxidant for the Conversion of Primary and Secondary Alcohols to Aldehydes and Ketones," Journal of Organic Chemistry (1983) 84:4155-4156 (English language on pp. 2-3 of document).
Author unknown, Encyclopedia of Cellulose, Asakura Publishing Co., Ltd., pp. 155-156 (Nov. 10, 2000).
Bakke, M. et al., "Identification, characterization, and molecular cloning of a novel hyaluronidase, a member of glycosyl hydrolase family 16, from *Penicillium* spp.," FEBS Letters (2011) 585(1):115-120.
Banerji, S. et al., "Structures of the Cd44-hyaluronan complex provide insight into a fundamental carboxyhydrate-protein interaction," Nature structural and molecular biology (2007) 14:234-239.
Benedetti, L. et al., "Biocompatibility and biodegradation of different hyaluronan derivatives (Hyaff) implanted-in rats," Biomaterials 1993, 14 (15), 1154-1160.
Bezakova, Z. et al., "Effect of microwave irradiation on the molecular and structural properties of hyaluronan," Carbohydrate Polymers, vol. 73, No. 4, 2008, pp. 640-646.
Boyer, I.J., "Toxicity of dibutyltin, tributyltin and other organotin compounds to humans and to experimental animals," Toxicology (1989) 55(3), 253-298.
Burdick, J.A. et al., "Controlled Degradation and Mechanical Behavior of Photopolymerized Hyaluronic Acid Networks," Biomacromolecules (2005) 6:386-391.
Burdick, J.A. et al., "Hyaluronic Acid Hydrogels for Biomedical Applications," Adv. Mater. (2011) 23:H41-H56.
Burke, J., Solubility Parameters: Theory and Application, The Book and Paper Group Annual, vol. Three, 1984, 62 pgs.
Burner, U. et al., Transient-state and steady-state kinetics of the oxidation of aliphatic and aromatic thiols by horseradish peroxidase, FEES Letters (1997) 411(2-3), 269-274.
Chen, L. et al., "Synthesis and pH sensitivity of carboxyymethyl chitosan-based polyampholyte hydrogel for protein carrier matrices," Biomaterials (2004) 25:3725-3732.
Cornwell, M.J. et al., "A one-step synthesis of cyclodextrin monoaldehydes," Tetrahedron Letters, vol. 36, No. 46, Nov. 13, 1995, pp. 8371-8374.
Crescenzi, V. et al., "Novel Hydrogels via Click Chemistry: Synthesis and Potential Biomedical Applications," Biomacromolecules (2007) 8:1844-1850.
Czech Official Action in Czech Patent Application No. PV 2008-705, dated Oct. 23, 2009, 2 pgs.
Czech Official Action in Czech Patent Application No. PV 2009-835, mailed Aug. 4, 2010, 2 pages.
Czech Official Action in Czech Patent Application No. PV 2009-836, mailed Aug. 6, 2010, 2 pages.
Czech Search Report in Czech Patent Application No. PV 2010-1001, dated Sep. 27, 2011, 1 pg.
Czech Search Report in Czech Patent Application No. PV 2011-241, dated Nov. 30, 2011, 1 pg.
Czech Search Report in Czech Patent Application No. PV 2012-136, dated Sep. 18, 2012, 3 pgs.
Czech Search Report in Czech Patent Application No. PV 2012-282, dated Jan. 30, 2013, 1 pg.
Czech Search Report in Czech Patent Application No. PV 2012-306, dated Feb. 11, 2013, 1 pg.
Czech Search Report in Czech Patent Application No. PV 2012-664, dated May 24, 2013, 3 pgs.
Czech Search Report in Czech Patent Application No. PV 2012-842, dated Aug. 19, 2013, 3 pgs.
Czech Search Report in Czech Patent Application No. PV 2012-843, dated Aug. 20, 2013, 1 pg.
Darr, A. et al., "Synthesis and characterization of tyramine-based hyaluronan hydrogels," Journal of Materials Science: Materials in Medicine (2009) 20(1), 33-44.
Dilling, W.L. et al., "Organic Photochemistry. XII. The Photodimerization and Photoisomerization of 2-Pyridone and Its Monochloro Derivatives," Mol. Photochem. (1973) 5(4):371-409.
Ding, B. et al., "TEMPO-mediated selective oxidation of substituted polysaccharides—an efficient approach for the determination of the degree of substitution at C-6", Carbohydrate Research, vol. 343, No. 18, Dec. 8, 2008, pp. 3112-3116.
Donati, A. et al., "Solution Structure of Hyaluronic Acid Oligomers by Experimental and Theoretical NMR, and Molecular Dynamics Simulation," Biopolymers vol. 59, 2001, pp. 434-445.
Dumitriu, S., "Characterization and Properties of Hyaluronic Acid (Hyaluronan)," by M. Milas et al., Chap. 22 of Polysaccharides: Structural Diversity and Functional Versatility, 1998, Marcel Dekker Inc., pp. 535-549.
Dunford, H. B. et al., "Kinetics of the oxidation of p-aminobenzoic acid catalyzed by horseradish peroxidase compounds I and II," J Biol Chem 1975, 250(8), 2920-32.
Eenschooten, C. et al., Preparation and structural characterisation of novel and versatile amphiphilic octenyl succinic anhydride-modified hyaluronic acid derivatives, Carbohydrate Polym ers, vol. 79, No. 3, 2010, pp. 597-605.
El-Sherbiny, I.M. et al., "Poly(ethylene glycol)-carboxymethyl chitosan-based pH-responsive hydrogels: photo-induced synthesis, characterization, swelling, and in vitro evaluation as potential drug carriers," Carbohydrate Research (2010) 345:2004-2012.
Elander, R.P., "Industrial production of β-lactam antibiotics," Applied Microbiology and Biotechnology (2003) 61:385-392.
European First Official Action in European Patent Application No. 10812840.6-1306, mailed Jul. 2, 2013, 10 pages.
European Second Official Action in European Patent Application No. 10812840.6-1306, mailed Sep. 24, 2014.
Feng, Qian et al., "Self-Assembly Behaviour of Hyaluronic Acid on Mica by Atomic Force Microscopy," vol. 20, No. 1, 2004, pp. 146-148 and 152 (English language Abstract p. 152).
Ferrero, C. et al., "Fronts movement as a useful tool for hydrophilic matrix release mechanism elucidation," International Journal of Pharmaceutics (2000) 202:21-28.
Ferruti, P. et al., "Novel Poly(amido-amine)-Based Hydrogels as Scaffolds for Tissue Engineering," Macromol. Biosci. (2005) 5:613-622.
Funakoshi, T. et al., "Novel chitosan-based hyaluronan hybrid polymer fibers as a scaffold in ligament tissue engineering," Journal of Biomedical Materials Reasearch, Part A, vol. 74A, No. 3, 2005, pp. 338-346.
Ghan, R. et al., "Enzyme-Catalyzed Polymerization of Phenols within Polyelectrolyte Microcapsules," Macromolecules (2004) 37(12), 4519-4524.
Gibby, W.A., "Cross-Linked DTPA Polysaccharides for Magnetic Resonance Imaging, Synthesis and Relaxation Properties," Invest. Radiol. 1989, vol. 24, pp. 302-309.
Gilabert, M. A. et al., "Differential substrate behaviour of phenol and aniline derivatives during oxidation by horseradish peroxidase: kinetic evidence for a two-step mechanism," Biochim Biophys Acta 2004, 1699 (1-2), 235-43.
Gilabert, M. A. et al., "Kinetic characterization of phenol and aniline derivates as substrates of peroxidase," Biol Chem 2004, 385 (9), 795-800.
Smeds, K.A. et al., "Photocrosslinkable polysaccharides for in situ hydrogel formation," J. Biomed. Mater. Res. (2001) 54:115-121.
Smejkalova, D. et al., "Structural and conformational differences of acylated hyaluronan modified in protic and aprotic solvent system," Carbohydrate Polymers (2012) 87(2):1460-1466.
Staskus, P.W. et al., "Double-Stranded Structure for Hyaluronic Acid in Ethanol-Aqueous Solution As Revealed by Circular Dichroism of Oligomers," Biochemistry vol. 27, No. 5, 1988, pp. 1528-1534.

(56) References Cited

OTHER PUBLICATIONS

Svanovsky, E. et al., "The effect of molecular weight on the biodistribution of hyaluronic acid radiolabeled with 111-In after intravenous administration to rats," Eur. J. Drug Metab. Ph. 2008, vol. 33, No. 3, pp. 149-157.
Tan, H. et al., Injectable in situ forming biodegradable chitosan-hyaluronic acid based hydrogels for cartilage tissue engineering. Biomaterials 2009, 30 (13), 2499-2506.
Tankam, P.F. et al., "Alkynyl polysaccharides: synthesis of propargyl potato starch followed by subsequent derivatizations," Carbohydrate Research (2007) 342:2049-2060.
Tao, Y. et al., Core cross-linked hyaluronan-styrylpyridinium micelles as a novel carrier for paclitaxel. (2012). Carbohydrate Polymers, 88(1), 118-124.
Testa, G. et al., "Influence of dialkyne structure on the properties of new click-gels based on hyaluronic acid," International Journal of Pharmaceutics (2009) 378:86-92.
Til, H.P. et al., Acute and Subacute Toxicity of Tyramine, Spermidine, Spermine, Putrescine and Cadaverine in Rats. Food and Chemical Toxicology (1997) 35(3-4), 337-348.
Tonelli, A. E., Effects of crosslink density and length on the number of intramolecular crosslinks (defects) introduced into a rubbery network. Polymer 1974, 15 (4), 194-196.
Tornoe, C. et al., "Peptidotriazoles on Solid Phase: [1,2,3]-Triazoles by Regiospecific Copper(I)-Catalyzed 1,3-Dipolar Cycloadditions of Terminal Alkynes to Azides," J. Org. Chem. (2002) 67:3057-3064.
Um, I.C. et al., "Electro-Spinning and Electro-Blowing of Hyaluronic Acid," Biomacromolecules (2004) 5:1428-1436.
Uyama, H. et al., Enzymatic Synthesis of Polyphenols. Current Organic Chemistry 2003, 7, 1387-1397.
van Bommel, K.J.C. et al., "Responsive Cyclohexane-Based Low-Molecular-Weight Hydrogelators with Modular Architecture," Angew. Chem. Int. Ed. (2004) 1663-1667.
Veitch, N.C., Horseradish peroxidase: a modem view of a classic enzyme. Phytochemistry 2004, 65 (3), 249-259.
Wang, J. et al., "Polymeric Micelles for Delivery of Poorly Soluble Drugs: Preparation and Anticancer Activity In Vitro of Paclitaxel Incorporated into Mixed Micelles Based on Polyethylene Glycol)-Lipid Conjugate and Positively Charged Lipids," Journal of Drug Targeting (2005) 13(1), 73-80.
Wang, X. et al., "Formation of water-resistant hyaluronic acid nanofibers by blowing-assisted electro-spinning an dnon-toxic post treatments," Polymer vol. 46, No. 13, 2005, pp. 4853-4867.
Weng, L. et al., "In vitro and in vivo suppression of cellular activity by guanidinoethyl disulfied released from hydrogel microspheres composned of partially oxidized hyaluronan and gelatin", Biomaterials, Aug. 3, 2008, vol. 29, pp. 4149-4156.
Weng, L. et al., "Self-crosslinkable hydrogels composed of partially oxidized hyaluronan and gelatin: In vitro and in vivo responses", Journal of Biomedical Materials Research Part A, Aug. 9, 2007, pp. 352-365.
Won, K. et al., "Horseradish Peroxidase-Catalyzed Polymerization of Cardanol in the Presence of Redox Mediators," Biomacromolecules (2003) 5(1), 1-4.
Written Opinion in International Patent Application No. PCT/CZ2009/000131, mailed Apr. 9, 2010, 3 pgs.
Written Opinion in International Patent Application No. PCT/CZ2010/000030, mailed Sep. 1, 2010, 4 pgs.
Written Opinion in International Patent Application No. PCT/CZ2011/000126, mailed Apr. 12, 2012, 4 pgs.
Written Opinion in International Patent Application No. PCT/CZ2012/000035, mailed Aug. 28, 2012, 4 pgs.
Written Opinion in International Patent Application No. PCT/CZ2013/000023, mailed Aug. 9, 2013, 3 pgs.
Written Opinion in International Patent Application No. PCT/CZ2013/000155, mailed Feb. 19, 2014, 6 pgs.
Written Opinion in International Patent Application No. PCT/CZ2013/000156, mailed Apr. 4, 2014, 7 pgs.
Written Opinion in International Patent Application No. PCT/CZ2013/000157, mailed Mar. 19, 2014, 6 pgs.
Written Opinion in International Patent Application No. PCT/CZ2013/000158, mailed Mar. 19, 2014, 7 pgs.
Xu, Y.-P. et al., "Kinetics of phenolic polymerization catalyzed by peroxidase in organic media," Biotechnology and Bioengineering 1995, 47 (1), 117-119.
Yamane, Shintaro et al., "Feasibility of chitosan-based hyaluronic acid hybrid biomaterial for a novel scaffold in cartilage tissue engineering," Biomaterials vol. 26, No. 6, 2005, pp. 611-619.
Yao, F. et al., "A Novel Amphoteric, pH-Sensitive, Biodegradable Poly[chitosan-g-(L-lactic-co-citric) acid] Hydrogel," Journal of Applied Polymer Science (2003) 89:3850-3854.
Yeom, J. et al., "Effect of Cross-Linking Reagents for Hyaluronic Acid Hydrogel Dermal Fillers on Tissue Augmentation and Regeneration," Bioconjugate Chemistry (2010) 21(2):240-247.
Zhong, S.P. et al., "Biodegradation of hyaluronic acid derivatives by hyalurondiase," Biomaterials vol. 15, No. 5, 1994, pp. 359-365.
Kuo, J.W., "Practical Aspects of Hyaluronan Based Medical Products," 2006, CRC Press, Taylor & Francis Group, pp. 60-61.
Lapcik, L. Jr. et al., Chemicke Listy vol. 85, 1991, pp. 281-298.
Leach, J.B. et al., "Characterization of protein release from photocrosslinkable hyaluronic acid-polyethylene glycol hydrogel tissue engineering scaffolds," Biomaterials (2005) 26:125-135.
Leach, J.B. et al., "Photocrosslinked Hyaluronic Acid Hydrogels: Natural, Biodegradable Tissue Engineering Scaffolds," Biotechnol Bioeng. (2003) 82:578-589.
Lee, F. et al., "An injectable enzymatically crosslinked hyaluronic acid-tyramine hydrogel system with independent tuning of mechanical strength and gelation rate," Soft Matter 2008, 4, 880-887.
Lee, K.Y. et al., "Electrospinning of polysaccharides for regenerative medicine," Advanced Drug Delivery Reviews (2009) 61:1020-1032.
Lee, S.A. et al., Spectroscopic studies of the physical properties of hyaluronate films: the origin of the phase transition; Carbohydrate Polymers; 1995; 28; 61-67.
Li, J. et al., "Redox-sensitive micelles self-assembled from amphiphilic hyaluronic acid-deoxycholic acid conjugates for targeted intracellular delivery of paclitaxel," Biomaterials (2012) 33(7), 2310-2320.
Linhardt, R.J. et al., "Polysaccharide lyases," Applied Biochemistry and Biotechnology (1986) 12:135-176.
Linhartova, B., Nanovlakna na bazi hyaluronanu, Bakalarska prace, Vysoke uceni technicke v Brne, 2008 (English language Abstract on p. 3).
Liu, Yanchun et al., "Biocompatibility and stability of disulfide-crosslinked hyaluronan films," Biomaterials vol. 26, No. 23, 2005, pp. 4737-4746.
Liu, Yanhua et al., Dual targeting folate-conjugated hyaluronic acid polymeric micelles for paclitaxel delivery, International Journal of Pharmaceutics, vol. 421, No. 1, 2011, pp. 160-169.
Luo, Yanfeng et al., "Novel amphoteric pH-sensitive hydrogels derived from ethylenediaminetetraacetic dianhydride, butanediamine and amino-terminated poly(ethylene glycol): Design, synthesis and swelling behavior," European Polymer Journal (2011) 47:40-47.
Malkoch, M. et al., "Synthesis of well-defined hydrogel networks using Click chemistry," Chem. Commun. (2006) 2774-2776.
Matsushima, R. et al., "Photoreactions of Alkylated 2-Pyridones," J. Chem. Soc. Perkin Trans. 2 (1985) 1445-1448.
Mayol, L. et al., Amphiphilic hyaluronic acid derivatives toward the design of micelles for the sustained delivery of lydrophobic drugs, Carbohydrate Polymers, vol. 102, Feb. 1, 2014, pp. 110-116.
Mazzone, S. B., Mori, N., Bunnan, M., Palovich, M., Belmonte, K. E.. & Canning, B. J. (2006). Fluorescent styryl dyes FM 1-43 and FM2-10 are muscarinic receptor antagonists: intravital visualization of receptor occupancy. The Journal of Physiology, 575(1), 23-35.
McIntyre, J.E, "The Chemistry of Fibres," Studies in Chemistry No. 6, 1971, p. 15.
McTaggart, L.E. et al., "Assessment of polysaccharide gels as drug delivery vehicles," Int. J. Pharm. 1993, vol. 100, pp. 199-206.

(56) References Cited

OTHER PUBLICATIONS

Miller, R.J. et al., Chemistry and Biology of Hyaluronan : Medicinal Uses of Modified Hyaluronate. Elsevier Ltd. 2004. 505-528.
Nevell, T.P. et al., "Cellulose Chemistry and its Applications," 1985, John Wiley & Sons, pp. 455-479.
Oh, E.J. et al., "Target specific and long-acting delivery of protein, peptide, and nukleotide therapeutics using hyaluronic acid derivatives," J. Controlled Release vol. 141, 2010, pp. 2-12.
Pal, K. et al., "Biopolymers in Controlled-Release Delivery Systems," Modern Biopolymer Science (2009) 519-557.
Park, Y.D. et al., Photopolymerized hyaluronic acid-based hydrogels and interpenetrating networks, Biomaterials (2003) 24:893-900.
Patel, P. K.; Monda!, M. S.; Modi, S.; Behere, D. V., Kinetic studies on the oxidation of phenols by the horseradish peroxidase compound II. Biochim Biophys Acta 1997, 1339 (1), 79-87.
Piluso, S. et al., "Hyaluronic acid-based hydrogels crosslinked by copper-catalyzed azide-alkyne cycloaddition with tailorable mechanical properties," International Journal of Artificial Organs (2011) 34:192-197, Abstract.
Prestwich, G.D., "Biomaterials from Chemically-Modified Hyaluronan", internet article, Feb. 26, 2001, 17 pgs.
Prestwich, G.D., "Hyaluronic acid-based clinical biomaterials derived for cell and molecule delivery in regenerative medicine," Journal of Controlled Release (2011) 155:193-199.
Qiu, Y. et al., "Environment-sensitive hydrogels for drug delivery," Advanced Drug Delivery Reviews (2001) 53:321-339.
Rao, K.V.R. et al., "Influence of Molecular Size and Water Solubility of the Solute on its Release from Swelling and Erosion Controlled Polymeric Matrices," Journal of Controlled Release (1990) 12:133-141.
Remy, H., Anorganicka chemie II, Sntl Praha 1971, pp. 306-321.
Ritger, P.L. et al., "A Simple Equation for Description fo Solute Release I. Fickian and Non-Fickian Release from Non-Swellable Devices in the Form of Slabs, Spheres, Cylinders or Discs," Journal of Controlled Release (1987) 5:23-36.
Ritger, P.L. et al., "A Simple Equation for Description fo Solute Release II. Fickian and Anomalous Release from Swellable Devices," Journal of Controlled Release (1987) 5:37-42.
Rostovtsev, V.V. et al., "A Stepwise Huisgen Cycloaddition Process: Copper(I)-Catalyzed Regioselective 'Ligation' of Azides and Terminal Alkynes," Angew. Chem. Int. Ed. (2002) 41(14):2596-2599.
Rupprecht, A., Wet Spinning of Hyaluronic Acid. Preparation of Oriented Samples; Acta Chemica Scandinavica; 1979; 33; 779-780.
Sahiner, N. et aL, "Fabrication and characterization of cross-linkable hydrogel particles based on hyaluronic acid: potential application in volcal fold regeneration", Journal of Biomaterials Science, Polymer Edition, vol. 19, Issue 2, pp. 223-243.
Schante, C.E. et al., "Chemical modifications of hyaluronic acid for the synthesis of derivatives for a broad range of biomedical applications," Carbohydrate Polymers (2011) 85:469-489.
Scott, J.E. et al., "Periodate Oxidation of Acid Polysaccharides", Histochemie, Apr. 26, 1969, vol. 19, pp. 155-161.
Scott, J.E. et al., "Secondary and tertiary structures of hyaluronan in aqueous solution, investigated by rotary shadowing—electron microscopy and computer simulation," J. Biochem vol. 274, 1991, pp. 699-705.
Sedova, P. et al., "Preparation of hyaluronan polyaldehyde—a precursor of biopolymer conjugates," Carbohydrate Research (2013) 371:8-15.
Seidlits, S.K. et al., "The effects of hyaluronic acid hydrogels with tunable mechanical properties on neural progenitor cell differentiation" Biomaterials (2010) 31:3930-3940.
Shang, J. et al., "Chitosan-based electroactive hydrogel," Polymer (2008) 49:5520-5525.
Sheehan, J.K. et al., X-ray diffraction studies on the connective tissue polysaccharides; J. Mol. Biol. 1975; 91; 153-163.
Shen, Y. et al., Synthesis and characterization of low molecular weight hyaluronic acid-based cationic micelles for efficient siRNA delivery, Carbohydrate Polymers, vol. 77, No. 1, 2009, pp. 95-104.

Shimizu, M. et al., "Studies on hyaluronidase, chondroitin sulphatase, proteinase and phospholipase secreted by *Candida* species," MYCOSES (1996) 39:161-167.
Shutava, T. et al., "Microcapsule modification with peroxidase-catalyzed phenol polymerization," Biomacromolecules 2004, 5 (3), 914-21.
Sieburth, S.M. et al., "Fusicoccin Ring System by [4+4} Cycloaddition. 2. A Model Study," Tetrahedron Letters (1999) 40:4007-4010.
Sieburth, S.M. et al., "The [4+4] Cycloaddition and its Strategic Application in Natural Product Synthesis," Tetrahedron (1996) 52(18):6251-6282.
Slaughter, B.V. et al., Hydrogels in Regenerative Medicine. Advanced Materials 2009, 21 (32-33), 3307-3329.
Slezingrova, K. et al., "Synteza a charakterizace palmitoyl hyaluronanu," Chemicke Listy (2012) 106:554.
Aldrich, Chem Files Synthetic Methods Oxidation (English translation), May 2005, vol. 5, No. 1 pp. 1-11.
Author unknown, Encyclopedia of Cellulose (English translation), Asakura Publishing Co., Ltd., pp. 155-156 (Nov. 10, 2000).
Office Action in U.S. Appl. No. 13/512,484, mailed Oct. 1, 2015, 8 pgs.
Office Action in U.S. Appl. No. 13/512,484, mailed Sep. 11, 2014, 8 pgs.
Office Action in U.S. Appl. No. 13/514,759, mailed Jul. 30, 2015, 12 pgs.
Office Action in U.S. Appl. No. 13/514,759, mailed Sep. 24, 2014, 10 pgs.
Office Action in U.S. Appl. No. 13/977,181, mailed Jan. 22, 2016, 8 pgs.
Office Action in U.S. Appl. No. 14/113,527, mailed Feb. 12, 2016, 11 pgs.
International Searching Authority, Written Opinion of the International Searching Authority and International Search Report in corresponding Application No. PCT/CZ2013/000091, mailed Oct. 31, 2013 (6 pages).
Gilabert, M. A. et al., "Stereospecificity of horseradish peroxidase," Biol Chem 2004, 385 (12), 1177-84.
Gong, J. et al., "Polymeric micelles drug delivery system in oncology," Journal of Controlled Release (2012) 159(3), 312-323.
Guillaumie, F. et al., Comparative studies of various hyaluronic acids produced by microbial fermentation for potential topical ophthalmic applications. Journal of Biomedical Materials Research Part A; 2009; 1421-1430.
Gupta, P. et al., "Hydrogels: from controlled release to pH-respoonsive drug delivery," Drug Discovery Today (2002) 7 (10):569-579.
Hasegawa, T. et al., "'Click chemistry' on polysaccharides: a convenient, general, and monitorable approach to develop (1-3)-β-D-glucans with various functional appendages," Carbohydrate Research (2006) 341:35-40.
Hewson, W. D. et al., "Oxidation of p-cresol by horseradish peroxidase compound I," J Biol Chem 1976, 251 (19), 6036-42.
Hewson, W. D. et al., "Stoichiometry of the reaction between horseradish peroxidase and p-cresol," J Biol Chem 1976, 251(19), 6043-52.
Higashimura, H. et al., Oxidative Polymerization. John Wiley & Sons, Inc. Olefin Fibers (2002) 10:740-764.
Hocek, M., "Tvorba C-C A C-X Vazeb Cross-Coupling Reakcemi Katalyzovanymi Komplexy Prechodnych Kovu," Chem. Listy (2003) 97:1145-1150.
Hoffman, A.S., "'Intelligent' Polymers in Medicine and Biotechnology," Artificial Organs 19(5):458-467.
Hofmann, H. et al., "Conformational Changes of Hyaluronic Acid in Acid Medium," Albrecht Von Graefe's Archive for Clinical and Experimental Opthamology vol. 198, No. 1, 1976, pp. 95-100.
Holten, K.B. et al., "Appropriate Prescribing of Oral Beta-Lactam Antibiotics," American Family Physician (2000) 62(3):611-620.
Huerta-Angeles, G. et al., "Synthesis of highly substituted amide hyaluronan derivatives with tailored degree of substitution and their crosslinking via click chemistry," Carbohydrate Polymers (2011) 84:1293-1300.

(56) References Cited

OTHER PUBLICATIONS

Huh, K.M. et al., "Hydrotropic polymer micelle system for delivery of paclitaxel," Journal of Controlled Release (2005) 101:59-68.
Hynes, W.L. et al., "Hyaluronidases of Gram-positive bacteria," FEMS Microbiology Letters (2000) 183:201-207.
Inanaga, J. et al., A Rapid Esterification by Means of Mixed Anhydride and Its Application to Large-ring Lactonization, Bulletin of the Chemical Society of Japan, vol. 52, No. 7, 1979, pp. 1989-1993.
International Preliminary Report on Patentability in International Patent Application No. PCT/CZ2010/000128 issued on Feb. 5, 2013.
International Preliminary Report on Patentability in International Patent Application No. PCT/CZ2010/000129, mailed Jun. 12, 2012, 5 pgs.
International Search Report and Written Opinion in International Patent Application No. PCT/CZ2010/000128, mailed Jun. 9, 2011.
International Search Report and Written Opinion in International Patent Application No. PCT/CZ2013/000057, mailed Jul. 24, 2013, 7 pgs.
International Search Report and Written Opinion in International Patent Application No. PCT/CZ2013/000063, mailed Apr. 23, 2015, 16 pgs.
International Search Report and Written Opinion in International Patent Application No. PCT/CZ2013/000116, dated Jan. 28, 2014, 8 pgs.
International Search Report in International Patent Application No. PCT/CZ2009/000131, mailed Apr. 9, 2010, 3 pgs.
International Search Report in International Patent Application No. PCT/CZ2010/000030, mailed Sep. 1, 2010, 3 pgs.
International Search Report in International Patent Application No. PCT/CZ2010/000129, mailed Jun. 15, 2011, 3 pgs.
International Search Report in International Patent Application No. PCT/CZ2011/000126, mailed Apr. 12, 2012, 3 pages.
International Search Report in International Patent Application No. PCT/CZ2012/0000035, mailed Aug. 28, 2012, 3 pgs.
International Search Report in International Patent Application No. PCT/CZ2013/000023, mailed Aug. 9, 2013, 3 pgs.
International Search Report in International Patent Application No. PCT/CZ2013/000155, mailed Feb. 19, 2014, 4 pgs.
International Search Report in International Patent Application No. PCT/CZ2013/000156, mailed Apr. 4, 2014, 5 pgs.
International Search Report in International Patent Application No. PCT/CZ2013/000157, mailed Mar. 19, 2014, 3 pgs.
International Search Report in International Patent Application No. PCT/CZ2013/000158, mailed Mar. 19, 2014, 3 pgs.
Jacoboni, I., "Hyaluronic Acid by Atomic Force Microscopy," Journal of Structural Biology vol. 126, 1999, pp. 52-58.
Jahn, M. et al., "The reaction of hyaluronic acid and its monomers glucuronic acid and N-acetylglucosamine, with reactive oxygen species," Carbohydrate Research, 1999, vol. 321, pp. 228-234.
Japanese Official Action (English language translation) in Japanese Patent Application No. 2012-542355, mailed Oct. 17, 2014.
Japanese Official Action (English language translation) in Japanese Patent Application No. 2014-506754, dated Jan. 22, 2015, 2 pgs.
Japanese Official Action (including English language translation) in Japanese Patent Application No. 2012-542356, mailed Oct. 3, 2014, 8 pages.
Jia, X.Q. et al., "Synthesis and Characterization of in Situ Cross-Linkable Hyaluronic Acid-Based Hydrogels with Potential Application for Vocal Fold Regeneration," Macromolecules (2004) 37:3239-3248.
Jiang, B. et al., "Study on TEMPO-mediated selective oxidation of hyaluronan and the effects of salt on the reaction kinetics," Carbohydrate Research, Pergamon, GB, vol. 327, No. 4, Aug. 7, 2000, pp. 455-461.
Jin, R. et al., Enzyme-mediated fast in situ formation of hydrogels from dextran-tyramine conjugates. Biomaterials 2007, 28 (18), 2791-2800.
Job, D. et al., "Substituent effect on the oxidation of phenols and aromatic amines by horseradish peroxidase compound I," Eur J Biochem 1976, 66 (3), 607-14.
Jou, Chi-Hsiung et al., "Biocompatibility and Antibacterial Activity of Chitosan and Hyaluronic Acid Immobilized Polyester Fibers," Journal of Applied Polymer Science vol. 104, No. 1, 2007, pp. 220-225.
Juhlin, L, Hyaluronan in skin; Journal of Internal Medicine; 1997; 242; 61-66.
Kalyanaraman, B.; Felix, C. C.; Sealy, R. C., Peroxidatic oxidation of catecholamines. A kinetic electron spin resonance investigation using the spin stabilization approach. Journal of Biological Chemistry 1984, 259 (12), 7584-7589.
Katritzky, A.R. et al., "Cycloaddition Reactions of Heteroaromatic Six-Membered Rings," Chem. Rev. (1989) 89:827-861.
Kawaguchi, Y. et al., "The relation between the adsorption behavior at the interface and the conformational changes in hyaluronates partially modified with various acyl chains," Carbohydrate Polymers (1995) 26:149-154.
Kedar, U. et al., Advances in polymeric micelles for drug delivery and tumor targeting, Nanomedicine Nanotechnology, Biology and Medicine, vol. 6, No. 6, 2010, pp. 714-729.
Kim, B. et al., "Complexation Phenomena in pH-Responsive Copolymer Networks with Pendent Saccarides," Macromol. (2002) 35:9545-9550.
Kim, T.G., Lee, H., Jang, Y., & Park, T. G. (2009). Controlled Release of Paclitaxel from Heparinized Metal Stent Fabricated by Layer-by-Layer Assembly of Polylysine and Hyaluronic Acid-g-Poly(lactic-co-glycolic acid) Micelles Encapsulating Paclitaxel. Biomacromolecules, 10(6), 1532-1539.
Korsmeyer, R.W. et al., "Mechanisms of solute release from porous hydrophilic polymers," International Journal of Pharmaceutics (1983) 15:25-35.

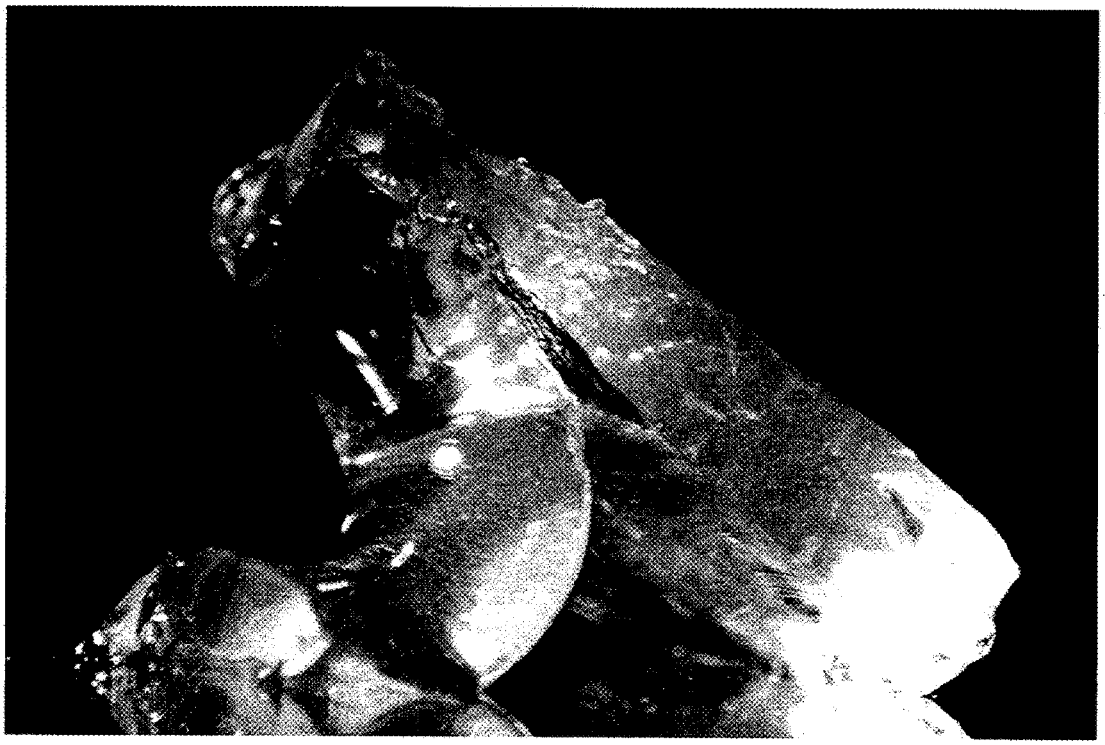

HYALURONIC ACID DERIVATIVE, METHOD OF PREPARATION THEREOF, METHOD OF MODIFICATION THEREOF AND USE THEREOF

FIELD OF THE ART

The invention relates to the preparation and use of a new hyaluronic acid derivative having a double bond in the positions 4 and 5 of the glucosamine part of the polysaccharide and an aldehydic group in the position 6 the glucosamine part of the polysaccharide chain, according to the formula X, or a hydrated form thereof with a geminal diole in the position 6 of the glucosamine part of the polysaccharide and a retained double bond in the positions 4 and 5 of the glucosamine part of the polysaccharide, according to the formula Y

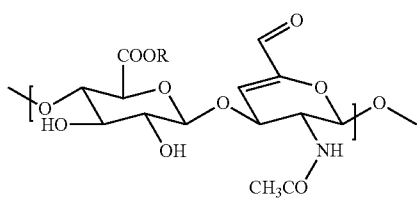

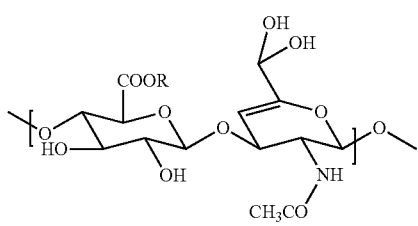

wherein R may be hydrogen, any metal cation or organic cation.

This unsaturated derivative of hyaluronan aldehyde is suitable for bonding of compounds containing an amino group, mainly in physiologic conditions. In case the bonded compound contains two or more amino groups, crosslinked materials may be prepared.

PRIOR ART

Hyaluronic acid is a glycosamino glycane composed of two repeating units of β-(1,3)-D-glucuronic acid and β-(1,4)-N-acetyl-D-glucosamine.

Scheme 1. Hyaluronic acid

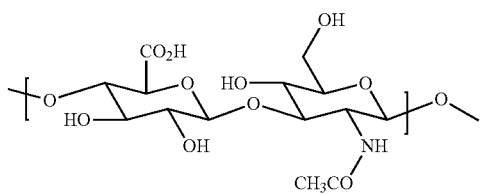

It is characterized by a high molecular weight of $5 \cdot 10^4$ to $5 \cdot 10^6$ g·mol$^{-1}$ which depends on the way of isolation thereof and on the starting material. This very hydrophilic polysaccharide is water-soluble in the form of a salt within the whole pH range. It is a part of the connective tissue, skin, joint synovial fluid, it plays an important role in a number of biological processes such as hydration, organization of proteoglycanes, cell differentiation, proliferation and angiogenesis. Since this polymer is body-natural, and therefore, biodegradable, it becomes a suitable substrate for tissue engineering or a carrier of biologically active substances.

Modification of Hyaluronic Acid to HA-Aldehyde

Most often, HA-aldehyde is prepared by a selective oxidation of the native hyaluronan. Oxidation of polysaccharides is a process in which the degree of oxidation of the functional groups of the polysaccharide is changed. In case of formation of an aldehyde the degree of oxidation increases formally by one degree. Carboxylic groups (oxidation by two degrees) form often as well, which may be a by-product of the oxidation to an aldehyde. In case of hyaluronic acid several approaches to the preparation of hyaluronan having an aldehydic group bonded thereto (HA-aldehyde) are known. These hyaluronan derivatives are one of the most used precursors for the preparation of biomaterials from a chemically modified hyaluronan. The main reason is that aldehydic groups are very stable in physiological conditions but at the same time they are still reactive enough for a fast and effective chemical reaction e.g. with amines.

The main methods of preparation of HA-aldehydes are shown in the following scheme 2.

Scheme 2

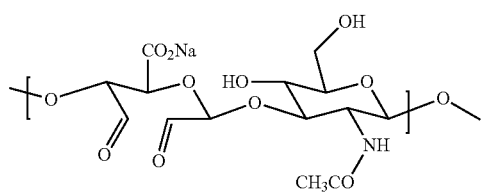

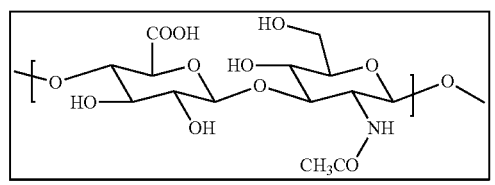

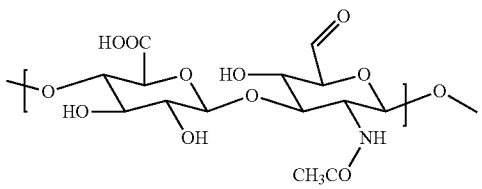

2

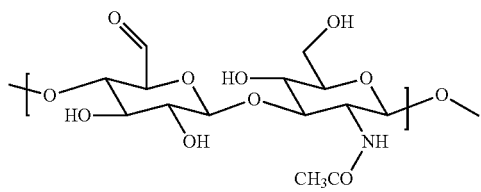

4

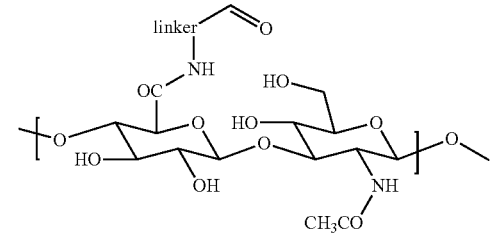

3

By far the most frequent method of introduction of an aldehydic group on hyaluronan is oxidation by means of NaIO$_4$ in water (Scheme 2, structure 1) (Spiro Robert et al.: WO 99/01143, Aeschlimann Daniel, Bulpitt Paul: WO 2007/0149441). This modification leads to opening of the saccharidic cycle and forming of two aldehydic groups.

Another method is oxidation of the primary hydroxylic group in the position 6 of the glucosamine part of the polysaccharide to an aldehyde (Scheme 2, structure 2) by means of the system NaClO/TEMPO in water (Buffa R., Kettou S., Velebný V. et al. WO 2011/069475) or by means of Dess-Martin periodinane in DMSO (Buffa R., Kettou S., Velebný V. et al. WO 2011/069474). As opposed to the structure 1, the aldehydic group in this position maintains the rigidity of the polymer chain.

An interesting method of introduction of an aldehydic group on hyaluronan is the possibility of bonding this group via a linker (Scheme 2, structure 3). There are various approaches possible here, such as introducing a vicinal diol on the carboxylic group of hyaluronan via an amide and the subsequent oxidation of the diol by means of NaIO$_4$ which gives rise to an aldehyde bonded via a linker (Hilborn J. et al: WO 2010/138074). This strategy may be advantageous consisting in that the aldehydic group is sterically more accessible for optional further modifications.

Another patent application (Aeschlimann Daniel and Bulpitt Paul: WO 2007/0149441) mentions the possibility to prepare HA-aldehyde by means of reduction of the carboxylic group of hyaluronan, using the agent 9-BBN (9-borabicyclo[3,3,1]nonan). It results in hyaluronan having an aldehydic group in the position 6 of the glucuronic part of the polysaccharide (Scheme 2, structure 4).

Condensation of HA-Aldehyde with N—Nucleophiles

The main application advantage of the condensation of HA-aldehydes with N-nucleophiles (amines) is that it may be carried out in physiological conditions. Generally, this reaction is described by the following scheme 3:

Scheme 3.

$$HA-CHO \xrightarrow{H_2N-X} HA-CH=N-X$$

The hydrolytic stability of the resulting imine —CH=N— linkage depends to a great extent on the character of the group X. Provided that X is an atom which is not bearing any free electron pair, such as —CH$_2$— group, hydrolytically very unstable imine HA-CH=N—CH$_2$— is formed. Provided that X is an atom which is bearing a free electron pair, a hydrolytically more stable conjugate is formed (oxime HA-CH=N—O—, hydrazone semicarbazone HA-CH=N—NH—CO— and the like) in which the imine bond —CH=N— is stabilized by conjugation with the free electron pair of the atom X. Many patents are known that disclose bonding of amines having the general formula NH$_2$—X—, wherein X is nitrogen or oxygen, to hyaluronan oxidized to an aldehyde, and where the final materials are formed at physiologically acceptable conditions so that they are applicable for a wide range of biomedicine applications. The recent ones include the patent (Bergman K., et al: WO 2009/108100) where materials based on hyaluronic acid modified by electrophilic groups such as aldehyde, maleinimide, acrylate, acrylamide, methacrylate, methacrylamide, vinylsulphone and aziridine are claimed in general. Hydrazides, semicarbazides, thiosemicarbazides, aminooxy, thiol and β-aminothiol groups are mentioned as crosslinking nucleophiles. Another patent application (Hilborn J. et al: WO 2010/138074) is similar and discloses bonding of N, S or at the same time N and S nucleophiles directly to hyaluronan oxidized to an aldehyde by means of oxidation with sodium periodate.

In case X is an aliphatic carbon (Scheme 3), it is generally known that the resulting imines are not hydrolytically stable (the bond —C=N— doesn't have any partner for conjugation) and reversibly convert to the original aldehyde and amine (Buffa R., Kettou S., Velebný V. et al. WO 2011/069474). The situation is described in the Scheme 4.

Scheme 4

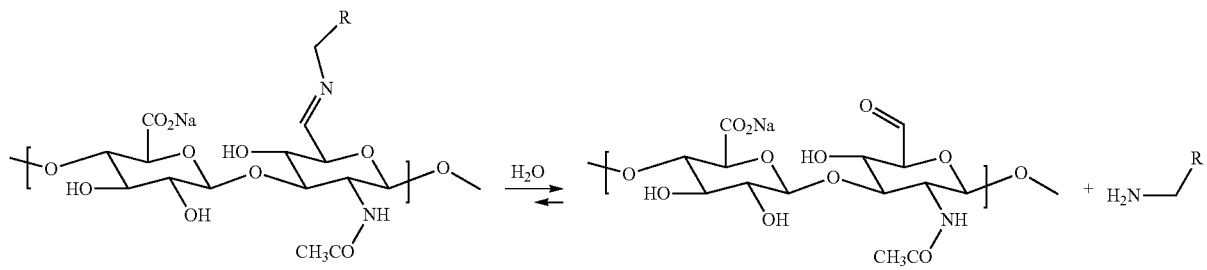

Another possibility how to stabilize said imines is to extend the conjugation from the other side, i.e. from the aldehyde side, which means providing the resulting imine with the conjugation having a multiple —C=C— bond. The general reaction is shown in Scheme 5.

Scheme 5.

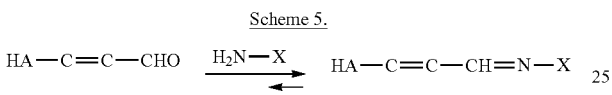

This approach is mentioned very rarely in literature, e.g. for reactions of aromatic aldehydes with amines, forming the so-called Schiff bases, where the stability is supported by the conjugation with an aromatic cycle Ar—CHO+H$_2$N—R→Ar—CH=N—R. However, in case of polysaccharides or polymers in general, no analogous example has been found. In such a modification of polymers, it would be necessary to introduce an aromatic group or, generally, any conjugated multiple bonds via a linker on the aldehyde, which is a technological complication and the biocompatibility of the material is not guaranteed. However, this method points to another potential complication. In case of presence of an aromatic system or more conjugated multiple bonds the material may absorb in the visible region already, therefore, the compound will be coloured which generally is not desirable (a possible photosensibility, complications in analytics in in vitro tests).

SUMMARY OF THE INVENTION

The subject-matter of the invention is hyaluronic acid of the general structural formula X or Y, which has some of its glucosamine cycles of the polysaccharide modified with a double bond in the positions 4 and 5 and at the same time an aldehydic group is present, or geminal diol (structure Y) in the position 6 of the glucosamine part of the polysaccharide

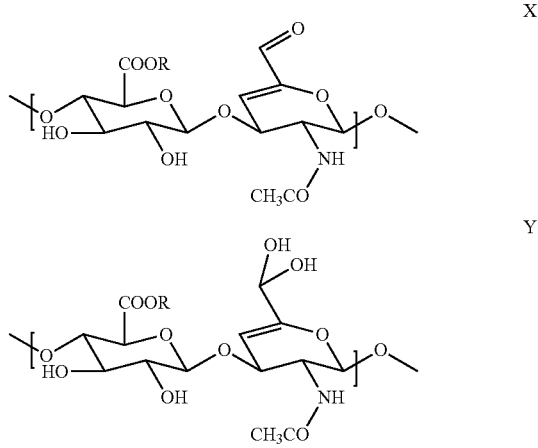

wherein R may be hydrogen, any metal cation or organic cation. Preferably, said derivative has the molecular weight within the range of 1 to 500 kDa. R is a sodium, potassium, calcium cation or an organic cation selected from the group comprising tetra $C_1$-$C_6$ alkylammonium, protonized $C_1$-$C_6$ alkylamine, preferably tetrabutyl ammonium or protonized triethylamine.

This solution allows stabilizing the hyaluronan conjugates with amino compounds by means of a multiple bond from the side of the aldehyde, so that practically any compound containing an amino group may be bonded to such modified hyaluronan in physiological conditions.

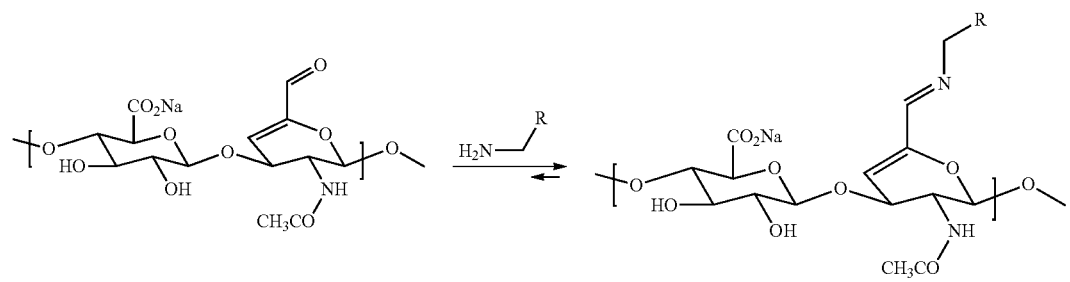

This is an important difference compared to saturated aldehydes of hyaluronan which are in physiological conditions able to strongly bond the compounds of the general formula H₂N—X—, wherein X is an atom bearing a free electron pair, usually oxygen or nitrogen. Since only very few natural substances contain the grouping H₂N—X—, the solution described in this patent application brings along a great advantage not only as a prospective carrier of biologically active substances but also in tissue engineering where very often hyaluronan derivatives crosslinked in physiological conditions with biologically acceptable amino compounds are used.

Further, the invention relates to the method of preparation of the derivative according to the structural formula X or Y, wherein first hyaluronic acid is oxidized to a HA-aldehyde in the position 6 of the glucosamine part (hereinafter referred to as Step 1), and then HA-aldehyde is dehydrated either in solution or by a simple heating in absence of solvents, bases or other additives (hereinafter referred to as Step 2). These two steps are explained in detail below:

Step 1: Selective oxidation of the primary hydroxyl group of hyaluronic acid in the position 6 of the glucosamine part of the polysaccharide to an aldehyde. The reaction may be carried out by means of e.g. the oxidation system 2,2,6,6-tetramethyl-1-piperidinyloxyl radical R¹-TEMPO/NaClO in water, wherein R¹ is hydrogen or the group N-acetyl:

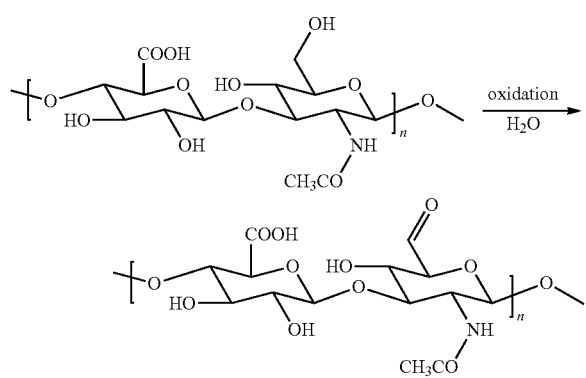

This step takes place preferably in water at the temperature −5 to 10° C., the molar amount of NaClO is within the range of 0.05 to 0.7 eq. and the molar amount of R¹-TEMPO is within the range of 0.005 to 0.2 eq. with respect to a dimer of hyaluronic acid. The starting hyaluronic acid may have the molecular weight within the range of 10 kDa to 5 MDa.

Step 2:
Variant 1: Dehydration of the HA-aldehyde in a polar aprotic solvent and water at the temperature of 30 to 80° C., preferably at 50 to 60° C., or
Variant 2: Heating of the pure saturated HA-aldehyde in dry state to the temperature of 50 to 100° C., preferably 70 to 80° C.

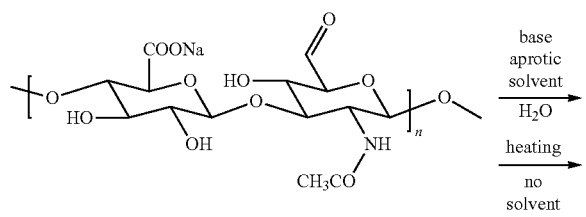

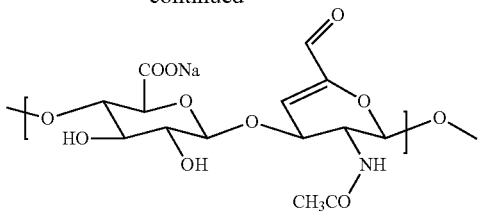

The first variant is dehydration in an aqueous-organic medium, wherein the organic solvent is water-miscible and the volume ratio solvent/water is within the range of 3/1 to 1/2. Preferably, in this step bases having limited nucleophilic properties, such as organic bases, e.g. triethylamine or N-diisopropyl-N-ethylamine, or inorganic bases, e.g. Ca(OH)₂ may be used. The amount of the base in the reaction is 0.01-20 equivalents with respect to a hyaluronan dimer, preferably 5-10 equivalents. The base may support elimination by cleaving a proton in alpha position of the aldehyde (position 5 of the cycle) and the resulting carbanion eliminates the hydroxy group in the position 4, forming a multiple bond. As organic solvents, aprotic polar solvents miscible with water may be used, preferably DMSO or sulfolan. The reaction is preferably carried out for 12 to 150 hours.

The second, technologically very attractive variant of realizing step 2 is to heat the starting saturated aldehyde in its dry state in absence of any additives to a higher temperature, preferably to the temperature of 70 to 80° C. for 12 hours to 10 days, preferably 4 to 5 days.

Further, the invention relates to the use of the unsaturated HA-aldehyde for bonding of amines. More specifically, the invention relates to the method of modification of the hyaluronic acid derivative according to the formula X or Y, wherein the derivative reacts with an amine according to the general formula H₂N—R², wherein R² is an alkyl, aromatic, heteroaromatic, linear or branched chain C₁-C₃₀, optionally containing N, S or O atoms. Said amine may be e.g. an amino acid, peptide or polymer containing a free amino group; wherein such polymer may be e.g. deacetylated hyaluronic acid, hyaluronic acid with an amino group bonded thereto via a linker, or gelatin, or another biologically acceptable polymer. The amount of amine, amino acid, peptide or free amino groups in the polymer is preferably within the range of 0.05 to 2 equivalents with respect to a hyaluronan dimer.

No specific conditions are required for the preparation of said conjugates. The reaction may take place in water, in phosphate buffer or in the system water-organic solvent at the temperature within the range of 20 to 60° C. for 10 minutes to 150 hours. The organic solvent may be selected from the group including water-miscible alcohols, especially isopropanol or ethanol, and water-miscible polar aprotic solvents, especially dimethyl sulfoxide, wherein the water content in the mixture is at least 50% vol. The reaction proceeds smoothly in physiological conditions, such as in phosphate buffer at pH=7.4 and the temperature 37° C., with a wide variety of amines, from simple amino acids to complicated peptides. In these conditions it is also possible to bond hydrazines, hydroxylamines, hydrazides, semicarbazides or thio semicarbazides without any problem. In case compounds containing two or more amino groups are bound, it is possible to prepare insoluble crosslinked derivatives having a wide variety of viscoelastic properties.

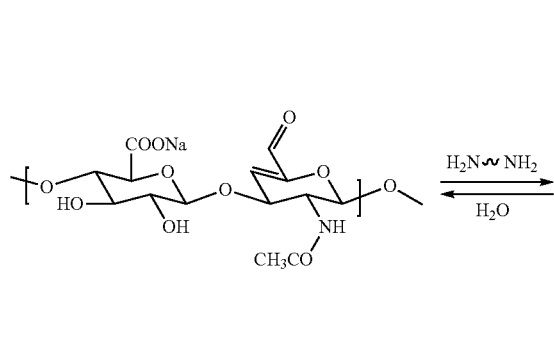 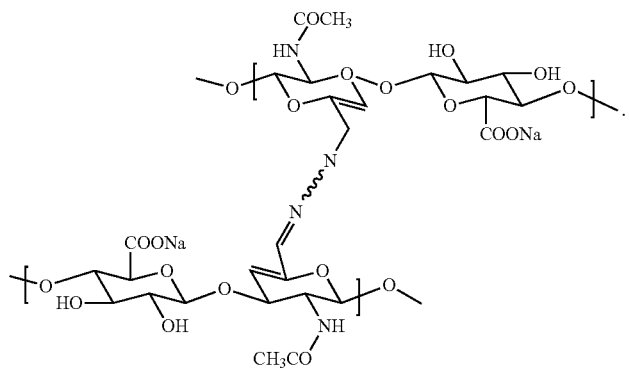

The higher stability of the bond of amine and unsaturated HA-aldehyde, compared to the saturated analogue thereof, allows preparation of more stable and better crosslinked insoluble biomaterials based on hyaluronan. This statement is described in greater detail in the part Examples, Example 21, wherein a saturated and an unsaturated derivative of HA-aldehyde having a similar substitution degree and molecular weight are compared in terms of the final rheologic properties for crosslinking with deacetylated hyaluronan.

Compared to the analogues mentioned in the part "Prior Art", the suggested method of modification is more advantageous in that it allows stronger bonding of considerably broader scale of amino group-containing compounds to hyaluronic acid in physiological conditions. This fact is a great advantage for application especially in tissue engineering where many biocompatible crosslinking amino-linkers may be used in physiological conditions even in presence of live cells. The modified derivatives may be used e.g. for the preparation of crosslinked materials and hydrogels, for the preparation of materials for tissue engineering or for biomedicinal applications. For crosslinking, also polysaccharides or amino groups-containing polymers in general may be used. Preferably, said invention may be used in the field of carriers of biologically active substances as well. The devised method allows immobilization of a wider range of biologically active amines (e.g. peptides) on hyaluronan, which may then be naturally released in native (active) form thereof. It has been found out that at a lower pH the bond amine-unsaturated HA-aldehyde is hydrolytically less stable and therefore the prepared conjugates may be used as pH-responsive materials as well (carriers, gels . . . ). It has been demonstrated that the unsaturated HA-aldehyde alone is not cytotoxic, and therefore, the conjugates thereof are a suitable candidate for various biomedicinal applications. Even though a person skilled in the art could expect that the conjugation from the aldehyde side with the —C═C— multiple bond would lead to a higher toxicity because e.g. acrolein $CH_2$═CH—CHO is a highly toxic and irritative substance, it is not so. The derivative according to the invention has a double bond right within the structure of the polymer (without any linker) and the final substrate has not exhibited any toxic properties. The derivatives according to the formula X or Y may be used for the preparation of materials having an anticancer effect, as carriers of biologically active substances in cosmetics and pharmacy or as carriers of biologically active substances with controlled release by means of changing the pH value.

The realization of the solution described in this application is not technologically complicated and does not require the use of expensive chemicals, solvents or isolation processes.

BRIEF DESCRIPTION OF DRAWINGS

FIG. 1 represents the elastic material prepared according to Example 20.

PREFERRED EMBODIMENTS OF THE INVENTION

DS=substitution degree=100%*(molar amount of the bound substituent or modified dimer)/(molar amount of all polysaccharide dimers)

The term equivalent (eq) as used herein means a hyaluronic acid dimer, if not indicated otherwise. The percentages are weight percentages, if not indicated otherwise.
The molecular weight of the initial hyaluronic acid (source: CPN spol. s.r.o., Dolní Dobrouč, CZ) is weight average and was determined by means of SEC-MALLS.

Example 1

Preparation of HA-Aldehyde Oxidized in the Position 6 of the Glucosamine Part

Oxidation of Hyaluronic Acid
Aqueous solution of NaClO (0.5 eq) was gradually added to a 1-percent aqueous solution of hyaluronan (1 g, 200 kDa) containing NaCl 1%, KBr 1%, TEMPO (0.01 eq) and $NaHCO_3$ (20 eq.), under nitrogen atmosphere. The mixture was stirred for 12 hours at the temperature of −5° C., then 0.1 g of ethanol was added and the mixture was stirred for another 1 hour. The resulting solution was then diluted by distilled water to 0.2% and dialyzed against the mixture (0.1% NaCl, 0.1% $NaHCO_3$) 3-times 5 liters (once a day) and against distilled water 7-times 5 liters (twice a day). Thereafter, the final solution was evaporated and analysed.
DS 10% (determined by NMR)
$^1$H NMR ($D_2O$) δ 5.26 (s, 1H, polymer-CH(OH)$_2$)
HSQC ($D_2O$) cross signal 5.26 ppm ($^1$H)-90 ppm ($^{13}$C) (polymer-CH(OH)$_2$)

Example 2

Dehydration of HA-Aldehyde 6.7 ml of DMSO and base DIPEA (5 eq) were added to a three-percent solution of HA-aldehyde (0.1 g, oxidation degree DS=10%, Example 1) in water. The mixture was stirred for 72 hours at the temperature of 40° C. The final solution was then precipitated by means of the mixture isopropanol/hexane and the solid fraction was dried in vacuum.

DS 6% (determined by NMR), Mw=110 kDa (determined by SEC MALLS)

$^1$H NMR (D$_2$O) δ 9.24 (s, 1H, —CH=O), 6.32 (m, 1H, —CH=C—CH=O)

UV-Vis (D$_2$O) 252 nm, π-π* transition of α,β-unsaturated aldehyde

Example 3

Dehydration of HA-Aldehyde 7.5 ml of DMSO and base DIPEA (5 eq) were added to a four-percent solution of HA-aldehyde (0.1 g, oxidation degree DS=10%, Example 1) in water. The mixture was stirred for 72 hours at the temperature of 50° C. The final solution was then precipitated by means of the mixture isopropanol/hexane and the solid fraction was dried in vacuum.

DS 5% (determined by NMR, more details in Example 2)

Example 4

Dehydration of HA-Aldehyde 2.5 ml of DMSO and base DIPEA (5 eq) were added to a two-percent solution of HA-aldehyde (0.1 g, oxidation degree DS=10%, Example 1) in water. The mixture was stirred for 72 hours at the temperature of 50° C. The final solution was then precipitated by means of the mixture isopropanol/hexane and the solid fraction was dried in vacuum.

DS 2% (determined by NMR, more details in Example 2)

Example 5

Dehydration of HA-Aldehyde 6.7 ml of sulfolan were added to a three-percent solution of HA-aldehyde (0.1 g, oxidation degree DS=10%, Example 1) in water. The mixture was stirred for 72 hours at the temperature of 60° C. The final solution was then precipitated by means of the mixture isopropanol/hexane and the solid fraction was dried in vacuum.

DS 1% (determined by NMR, more details in Example 2)

Example 6

Dehydration of HA-Aldehyde 6.7 ml of sulfolan and base Et$_3$N (5 eq) were added to a three-percent solution of HA-aldehyde (0.1 g, oxidation degree DS=10%, Example 1) in water. The mixture was stirred for 72 hours at the temperature of 50° C. The final solution was then precipitated by means of the mixture isopropanol/hexane and the solid fraction was dried in vacuum.

DS 5% (determined by NMR, more details in Example 2)

Example 7

Dehydration of HA-Aldehyde 6.7 ml of sulfolan and base DIPEA (2 eq) were added to a three-percent solution of HA-aldehyde (0.1 g, oxidation degree, Example 1) in water. The mixture was stirred for 12 hours at the temperature of 80° C. The final solution was then precipitated by means of the mixture isopropanol/hexane and the solid fraction was dried in vacuum.

DS 2% (determined by NMR, more details in Example 2)

Example 8

Dehydration of HA-Aldehyde 6.7 ml of sulfolan and base Ca(OH)$_2$ (1 eq) were added to a three-percent solution of HA-aldehyde (0.1 g, oxidation degree, Example 1) in water. The mixture was stirred for 150 hours at the temperature of 30° C. The final solution was then precipitated by means of the mixture isopropanol/hexane and the solid fraction was dried in vacuum.

DS 2% (determined by NMR, more details in Example 2)

Example 9

Dehydration of HA-Aldehyde

HA-aldehyde (0.1 g, oxidation degree DS=10%, Example 1) was heated in its solid state for 5 days at 80° C. Then it was analysed by means of NMR.

DS 3% (determined by NMR, more details in Example 2)

Example 10

Dehydration of HA-Aldehyde

HA-aldehyde (0.1 g, oxidation degree DS=10%, Example 1) was heated in its solid state for 12 hours at 100° C. Then it was analysed by means of NMR.

DS 2% (determined by NMR, more details in Example 2)

Example 11

Dehydration of HA-Aldehyde

HA-aldehyde (0.1 g, oxidation degree DS=10%, Example 1) was heated in its solid state for 10 days at 50° C. Then it was analysed by means of NMR.

DS 2% (determined by NMR, more details in Example 2)

Example 12

Bonding of Amines to α,β-Unsaturated HA-Aldehyde n-butylamine (2 eq) was added to a one-percent solution of unsaturated HA-aldehyde (0.1 g, substitution degree DS=6%, Example 2) in 0.1M aqueous phosphate buffer at pH of 7.4. The mixture was stirred for 5 hours at the temperature of 37° C. The final solution was then precipitated by means of the mixture isopropanol/hexane and the solid fraction was dried in vacuum.

DS 5% (determined by NMR)

$^1$H NMR (D$_2$O) δ 7.74 (s, 1H, —CH=N-Bu), 5.68 (m, 1H, —CH=C—CH=N-Bu)

HSQC (D$_2$O) cross signal 7.74 ppm ($^1$H)-158 ppm ($^{13}$C) —CH=N-Bu cross signal 5.68 ppm ($^1$H)-112 ppm ($^{13}$C) —CH=C—CH=N-Bu

Example 13

Bonding of Amines to α,β-Unsaturated HA-Aldehyde n-butylamine (0.05 eq) was added to a one-percent solution of unsaturated HA-aldehyde (0.1 g, substitution degree DS=6%, Example 2) in 0.1M aqueous phosphate buffer at pH of 7.4. The mixture was stirred for 150 hours at the temperature of 20° C. The final solution was then precipitated by means of the mixture isopropanol/hexane and the solid fraction was dried in vacuum.
DS 2% (determined by NMR, more details in Example 12)

Example 14

Bonding of Amines to α,β-Unsaturated HA-Aldehyde n-butylamine (0.3 eq) was added to a one-percent solution of unsaturated HA-aldehyde (0.1 g, substitution degree DS=6%, Example 2) in water. The mixture was stirred for 10 minutes at the temperature of 60° C. The final solution was then precipitated by means of the mixture isopropanol/hexane and the solid fraction was dried in vacuum.
DS 5% (determined by NMR, more details in Example 12)

Example 15

Bonding of Lysine to α,β-Unsaturated HA-Aldehyde

Lysine (0.3 eq) was added to a one-percent solution of unsaturated HA-aldehyde (0.1 g, substitution degree DS=6%, Example 2) in 0.1M aqueous phosphate buffer at pH of 7.4. The mixture was stirred for 24 hours at the temperature of 20° C. The final solution was then precipitated by means of the mixture isopropanol/hexane and the solid fraction was dried in vacuum.
DS 5% (determined by NMR)
$^1$H NMR (D$_2$O) δ 7.76 (s, 1H, —CH=N-lysine), 5.65 (m, 1H, —CH=C—CH=N-lysine)

Example 16

Bonding of Pentapeptide Pal-KTTKS (Palmitoyl-Lys-Thr-Thr-Lys-Ser) to α,β-Unsaturated HA-Aldehyde 5 ml of IPA and then the solution of substituted pentapeptide pal-KTTKS (0.1 eq) in 5 ml of isopropylalcohol were added to a one-percent solution of unsaturated HA-aldehyde (0.1 g, substitution degree DS=6%, Example 2) in 0.1M aqueous phosphate buffer at pH of 7.4. The mixture was stirred for 72 hours at the temperature of 20° C. The final solution was evaporated in a rotating vacuum evaporator to one third of the volume and then it was precipitated by means of the mixture of isopropanol/hexane and the solid fraction was dried in vacuum.
DS 1% (determined by NMR)
$^1$H NMR (D$_2$O) δ 7.75 (s, 1H, —CH=N-peptide), 5.66 (m, 1H, —CH=C—CH=N-peptide)

Example 17

Crosslinking of α,β-Unsaturated HA-Aldehyde by Lysine

One-percent solution of lysine in water (0.1 eq) was added to a five-percent solution of unsaturated HA-aldehyde (0.1 g, substitution degree DS=6%, Example 2) in 0.1M aqueous phosphate buffer at pH of 7.4. The mixture was stirred for 24 hours at the temperature of 20° C. An increase of viscosity of the final solution was observed.

Example 18

Crosslinking of α,β-Unsaturated HA-Aldehyde by Dihydrazide Adipate

One-percent solution of dihydrazide adipate in water (0.1 eq) was added to a five-percent solution of unsaturated HA-aldehyde (0.015 g, substitution degree DS=6%, Example 2) in 0.1M aqueous phosphate buffer at pH of 7.4. The mixture was stirred for 24 hours at the temperature of 20° C. An increase of viscosity of the final solution was observed.

Example 19

Preparation of Deacetylated Hyaluronan 65 ml of sulfolan were added to a three-percent solution of hyaluronan (1 g, 830 kDa) in hydrazine hydrate containing 30 g of hydrazine sulphate and the mixture was heated for 48 hours at 70° C. The final solution is diluted by distilled water to 0.2% and dialysed against the mixture (0.1% NaCl, 0.1% NaHCO$_3$) 3-times 5 liters (once a day) and against distilled water 7-times 5 liters (twice a day). The final solution was then evaporated and analysed.
DS 32% (determined by NMR), Mw 37 kDa (determined by SEC-MALLS)
$^1$H NMR (1% NaOD in D$_2$O) δ 2.75 (s, 1H, —CH—NH$_2$)

Example 20

Crosslinking of α,β-Unsaturated HA-Aldehyde by Means of Deacetylated Hyaluronan A three-percent solution of deacetylated hyaluronan (0.015 g, Example 19) in 0.1M aqueous phosphate buffer at pH of 7.4 (0.1 eq) was added to a three-percent solution of unsaturated HA-aldehyde (0.025 g, substitution degree DS=6%, Example 2) in 0.1M aqueous phosphate buffer at pH of 7.4. The mixture was stirred for 24 hours at the temperature of 20° C. An increase of viscosity of the final solution was observed.

Example 21

Comparison of Mechanical and Visco-Elastic Properties of Hydrogels Based on the Crosslinked α,β-Unsaturated HA-Aldehyde and the Crosslinked Saturated HA-Aldehyde crosslinking by deacetylated hyaluronan
Material 1: Unsaturated HA-aldehyde (0.06 g, DS=6%, Mw=110 kDa, Example 2) 3% solution in PBS pH 7.4+ deacetylated hyaluronan (0.02 g, Example 19) 3% solution in PBS pH 7.4.

Material 2: Saturated HA-aldehyde (0.06 g, DS=7%, Mw=100 kDa) 3% solution in PBS pH 7.4+deacetylated hyaluronan (0.02 g, Example 19) 3% solution in PBS pH 7.4.

Hydrogel samples were prepared from the above materials by mixing and a thorough homogenization of both components thereof (3% solution of unsaturated HA-aldehyde in PBS/3% solution of saturated HA-aldehyde and 3% solution of deacetylated hyaluronan in PBS). The samples were always left to mature for 240 minutes at room temperature, thereafter a homogenous transparent gel is formed. All samples were of the same proportions and were measured at constant laboratory conditions (temperature, pressure, humidity).

Mechanical properties of the samples were determined. More specifically, Compressive Young's modulus indicating the hardness/elasticity of the material, Modulus of Toughness indicating the resistance of the sample and what energy the material is able to absorb without occurring any permanent deformation. Further, the Compressive stress at Break indicating the maximum load that the material is able to absorb without occurring any permanent deformation, and, within the framework of visco-elastic properties, the Storage modulus in Shear loss angle.

| Material Number | Compressive Young's modulus (kPa) | Compressive stress at Break (kPa) | Modulus of Toughness (J/m³) | Storage modulus (Pa) | Shear loss angle δ (°) |
|---|---|---|---|---|---|
| 1 | 0.844 | 382.06 | 29690 | 160 | 2.36 |
| 2 | 0.482 | 309.29 | 19488 | 55 | 10.3 |

The results achieved within this Example demonstrate the advantageousness of the use of the unsaturated HA-aldehyde compared to the saturated HA-aldehyde with regard to the preparation of more rigid and more tenacious (better cross-linked) materials suitable for tissue engineering.

The invention claimed is:

1. Hyaluronic acid derivative modified by a double bond in the positions 4 and 5 of the glucosamine part of the polysaccharide and at the same time oxidized to an aldehyde in the position 6 of the glucosamine part of the polysaccharide, according to the structural formula X, or a hydrated form thereof according to the structural formula Y

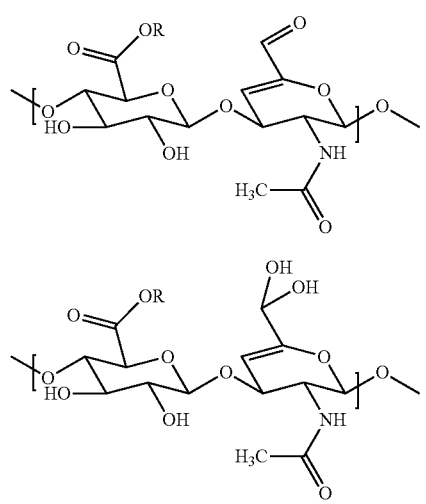

wherein R is hydrogen, any metal cation or an organic cation.

2. The hyaluronic acid derivative according to claim 1, characterized by that it has the molecular weight within the range of 1 to $5·10^5$ g·mol$^{-1}$ and R is a sodium, potassium, calcium cation or an organic cation which is selected from the group comprising tetra $C_1$-$C_6$-alkylammonium and protonized $C_1$-$C_6$-alkylamine.

3. The hyaluronic acid derivative according to claim 1, characterized by that it has the molecular weight within the range of 1 to $5·10^5$ g·mol$^{-1}$ and R is tetrabutyl-ammonium or protonized triethyl amine.

4. A method of preparation of the hyaluronic acid derivative defined in claim 1 characterized by that the hyaluronic acid oxidized to an aldehyde in the position 6 of the glucosamine part is dehydrated in the positions 4 and 5 of the glucosamine part in the mixture of water/polar aprotic solvent at the temperature 30 to 80° C.

5. The method of preparation according to claim 4 characterized by that the mixture further contains a base in the amount of 0.01 to 20 equivalents with respect to a hyaluronic acid dimer, wherein the base is selected from the group comprising organic bases or inorganic bases.

6. The method of preparation according to claim 4 characterized by that the aprotic solvent is water miscible and includes DMSO or sulfolan, and the volume ratio solvent/water is within the range of 3/1 to 1/2.

7. The method of preparation according to claim 4 characterized by that the reaction proceeds for 12 to 150 hours.

8. A method of preparation of the hyaluronic acid derivative defined in claim 1 characterized by that the hyaluronic acid oxidized to an aldehyde in the position 6 of the glucosamine part is dehydrated in the positions 4 and 5 of the glucosamine part in solid phase, without the use of solvents or other additives, by heating to the temperature of 50 to 100° C. for 12 hours to 10 days.

9. The method of preparation according to claim 4 or claim 8 characterized by that the initial hyaluronic acid has the molecular weight within the range of $1·10^4$ g·mol$^{-1}$ to $5·10^6$ g·mol$^{-1}$.

10. A method of modification of the hyaluronic acid derivative defined in claim 1 characterized by that the derivative reacts with an amine of the general formula $H_2N$—$R^2$ wherein $R^2$ is a $C_1$-$C_{30}$ alkyl, aromatic, heteroaromatic, linear or branched chain, optionally containing N, S or O atoms.

11. The method of modification of the hyaluronic acid derivative according to claim 10 characterized by that the derivative reacts with an amino acid or a peptide.

12. The method of modification of the hyaluronic acid derivative according to claim 10 characterized by that the derivative reacts with a polymer which contains a free amino group.

13. The method of modification of the hyaluronic acid derivative according to claim 12 characterized by that the polymer is deacetylated hyaluronic acid, hyaluronic acid with an amino group bonded thereto via a linker, or gelatin, or another biologically acceptable polymer.

14. The method of modification according to claim 10 characterized by that the amount of amine, amino acid, peptide or free amino groups of the polymer is within the range of 0.05 to 2 equivalents with respect to a hyaluronan dimer.

15. The method of modification according to claim 10 characterized by that the reaction with the amine, amino acid, peptide or polymer containing a free amino group takes place in water, in phosphate buffer or in a system water-organic solvent at the temperature within the range of 20 to 60° C. for 10 minutes to 150 hours.

16. The method of modification according to claim 15 characterized by that the organic solvent is selected from the group comprising water-miscible alcohols and water-miscible polar aprotic solvents, wherein the content of water in the mixture is at least 50% by volume.

* * * * *

UNITED STATES PATENT AND TRADEMARK OFFICE
CERTIFICATE OF CORRECTION

| | |
|---|---|
| PATENT NO. | : 9,522,966 B2 |
| APPLICATION NO. | : 14/420012 |
| DATED | : December 20, 2016 |
| INVENTOR(S) | : Radovan Buffa et al. |

Page 1 of 1

It is certified that error appears in the above-identified patent and that said Letters Patent is hereby corrected as shown below:

On the Title Page

Column 2,
In Formula X, "COOH" should be -- COOR --.
In Formula Y, "COOH" should be -- COOR --.

Page 3, Column 1,
Line 45, "carboxyymethyl" should be -- carboxymethyl --.

Page 4, Column 1,
Line 42, "Polyethylene Glycol)-" should be -- Poly(ethylene Glycol) --.
Line 46, "an dnon-toxic" should be -- and non-toxic --.
Line 50, "componsed of" should be -- composed of --.

Page 5, Column 1,
Line 17, "Monda!," should be -- Mondal, --.
Line 36, "fo" should be -- of --.
Line 40, "fo" should be -- of --.

In the Drawings

"FIG. 1" should appear underneath Figure 1.

In the Specification

Column 4,
Lines 40-41, "...formed (oxime HA-CH=N-O-, hydrazone semicarbazone HA-CH=N-NH-CO- and the like) in which the..." should be -- ...formed (oxime HA-CH=N-O-, hydrazone HA-CH=N-NH-, semicarbazone HA-CH=N-NH-CO- and the like) in which the... --.

Signed and Sealed this
Eighteenth Day of April, 2017

Michelle K. Lee
*Director of the United States Patent and Trademark Office*